United States Patent
Ubby et al.

(10) Patent No.: US 6,206,874 B1
(45) Date of Patent: Mar. 27, 2001

(54) APPARATUS AND METHOD FOR LOCATING ELECTRICALLY ACTIVE SITES WITH AN ANIMAL

(75) Inventors: Johan Ubby, West Port, CT (US); Gösta Sjöholm, Bromma (SE)

(73) Assignee: Siemens-Elema AB, Solna (SE)

( * ) Notice: Subject to any disclaimer, the term of this patent is extended or adjusted under 35 U.S.C. 154(b) by 0 days.

(21) Appl. No.: 09/287,003

(22) Filed: Apr. 6, 1999

(30) Foreign Application Priority Data

Apr. 8, 1998 (SE) .................................................... 9801238

(51) Int. Cl.$^7$ .................................................... A61B 18/04
(52) U.S. Cl. .............................. 606/34; 607/122; 600/508
(58) Field of Search ................................. 606/32, 34, 41, 606/42; 607/115, 116, 122; 600/374, 508, 509, 515, 546

(56) References Cited

U.S. PATENT DOCUMENTS

| | | | |
|---|---|---|---|
| 5,297,549 | * | 3/1994 | Beatty et al. ........................ 128/642 |
| 5,391,199 | | 2/1995 | Ben-Haim . |
| 5,433,198 | | 7/1995 | Desai . |
| 5,465,717 | | 11/1995 | Imram et al. . |
| 5,497,780 | | 3/1996 | Zehender . |
| 5,515,853 | | 5/1996 | Smith et al. . |
| 5,637,090 | * | 6/1997 | McGee et al. ........................ 604/95 |
| 5,722,402 | * | 3/1998 | Swanson et al. ..................... 128/642 |
| 5,817,030 | * | 10/1998 | Tarjan et al. ........................ 600/546 |
| 6,070,094 | * | 5/2000 | Swanson et al. ..................... 600/374 |

OTHER PUBLICATIONS

"Direction Independent Locally Specific Permanent Electrodes for the Identification of Arrhythmia," Tarjan, Abstract 491 from VIII$^{th}$ World Symposium on Cardiac Pacing (1987), PACE, vol. 10, May–Jun. 1987 Part II, p. 752.

* cited by examiner

*Primary Examiner*—Michael Peffley
(74) *Attorney, Agent, or Firm*—Schiff Hardin & Waite

(57) ABSTRACT

An apparatus for locating an electrically active site within an organ or other internal body structure has a number of electrical activity sensors positionable proximate a wall of the organ or internal body structure and relatively locatable. Each sensor produces an output indicative of the arrival of an electrical signal from the active site and a signal processing unit to utilize the series of outputs to determine, by triangulation, the location of the active site.

9 Claims, 2 Drawing Sheets

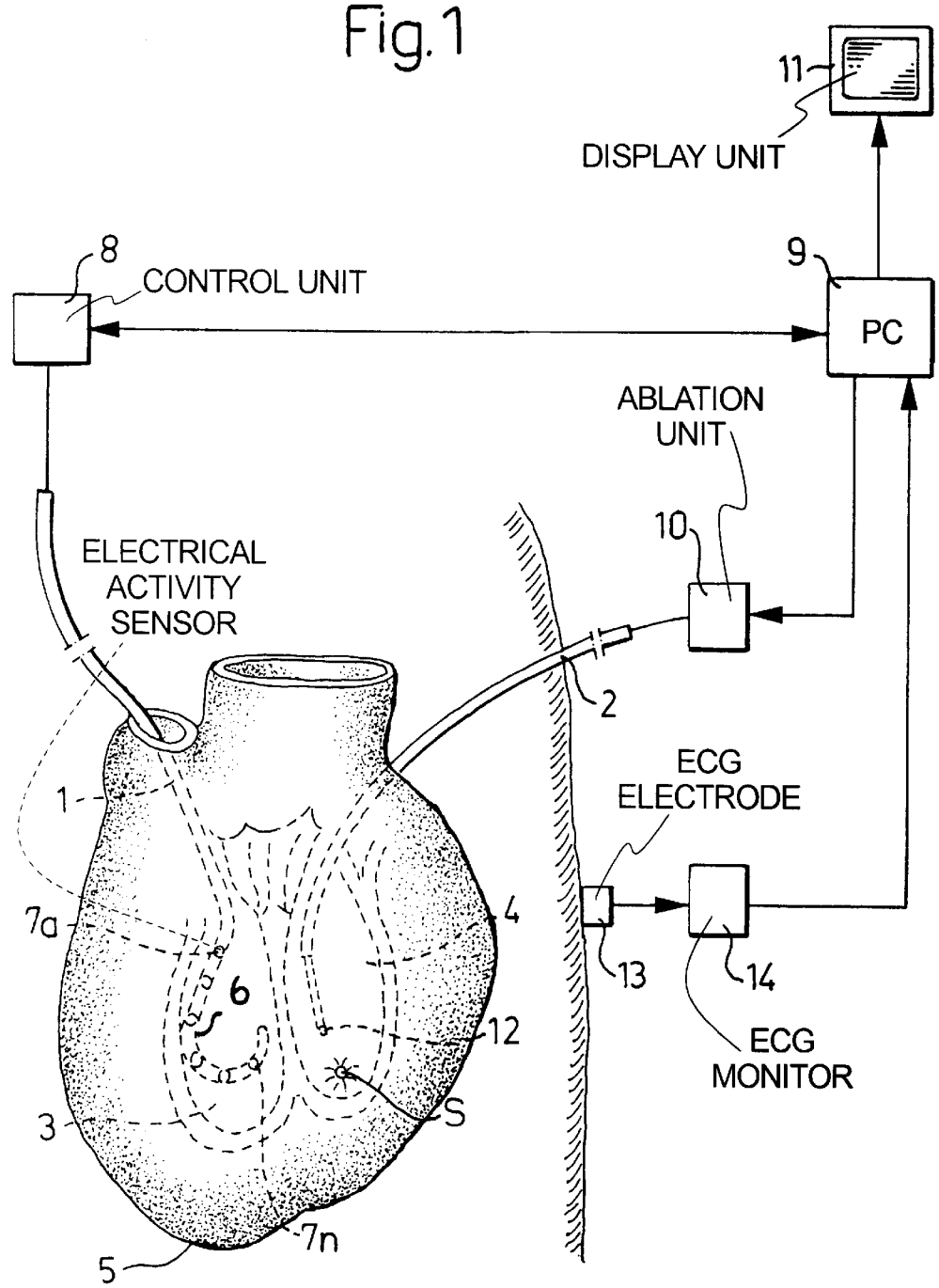

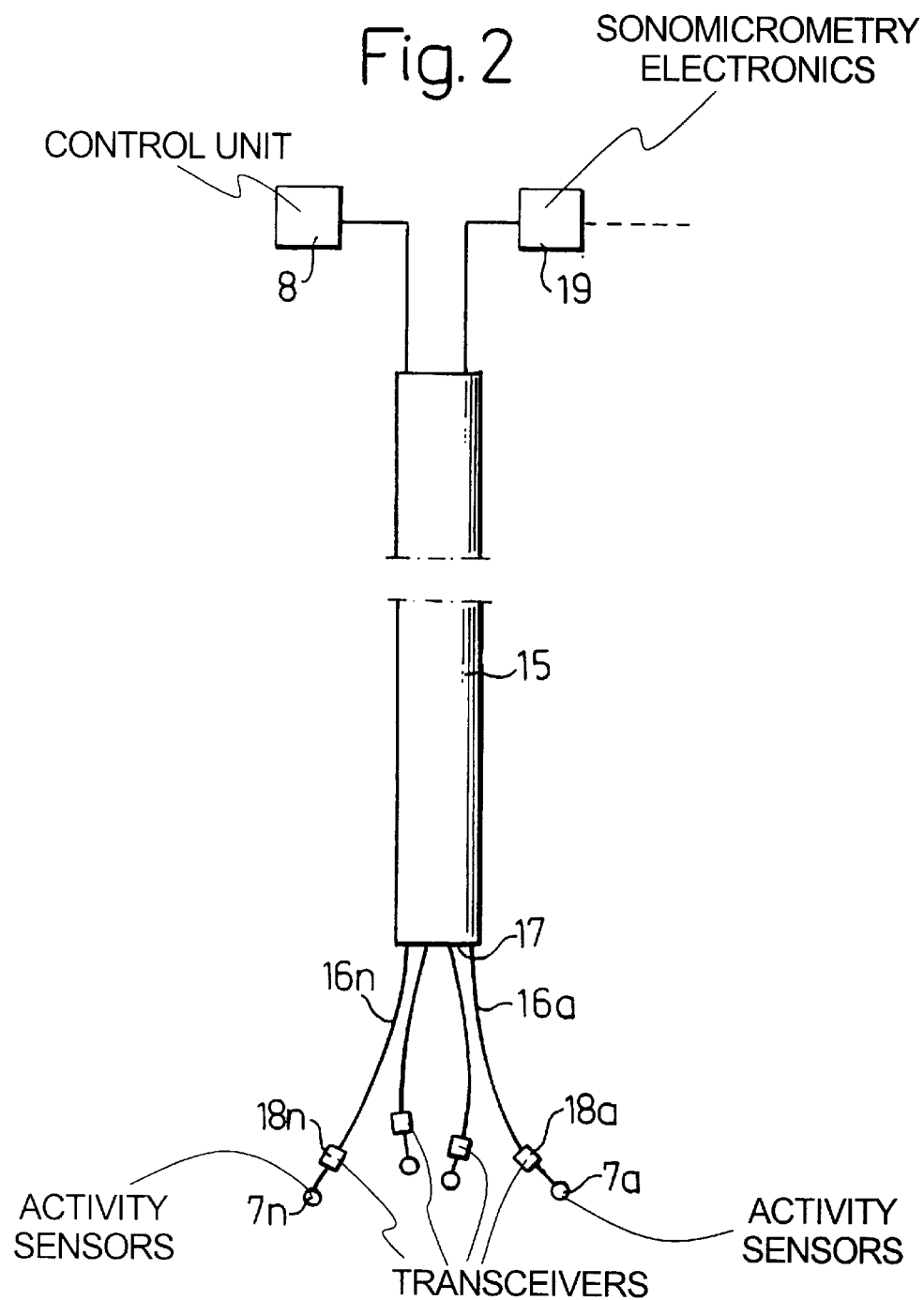

APPARATUS AND METHOD FOR LOCATING ELECTRICALLY ACTIVE SITES WITH AN ANIMAL

BACKGROUND OF THE INVENTION

1. Field of the Invention

The present invention relates to an apparatus and method for S locating electrically active sites within a heart or other organ or internal body structure of an animal. In particular the present invention relates to an apparatus and method for locating originating sites of cardiac arrhythmias in humans.

2. Description of the Prior Art

One of the most common type of cardiac arrhythmia is ventricular tachycardia (VT) which is typified by very rapid and ineffectual contractions of the heart muscle. In a majority of patients VT originates from a small (1–2 mm) lesion that is located close to the inner surface of the heart chamber. A known treatment of VT is mapping the electrical pathways of the heart, for example by recording arrival times of electrical pulses at numerous specific locations within the heart, and building up an isochronal activation map which may then be used to locate the lesion, i.e. the "active site", from which the mapped electrical signals originate. Once located, the site is physically ablated using an ablation catheter.

One known method and apparatus for treating cardiac arrhythmias is disclosed in U.S. Pat. No. 5,391,199 (Biosense Inc.) and has means for obtaining and displaying a perspective image of the organ to be mapped, a mapping catheter having a single mapping electrode and means to locate the distal tip of the catheter by triangulation, using non-ionizing radiation. The method involves repeatedly locating the distal tip of the catheter (and hence the site of the mapping electrode), displaying the local information from the electrode is at the correct location on the perspective image and advancing the electrode to a new site. After several repetitions an activation map is created from which the active site may be deduced. An ablation catheter is advanced to this site which is then ablated. A disadvantage with this apparatus is that the mapping catheter must be repositioned several times in order to construct the map. This is time consuming and may lead to errors since the local information usually has to be collected at the same point in the cardiac cycle each time.

A further known method and apparatus for cardiac mapping is described in U.S. Pat. No. 5,465,717 (Cardiac Pathways Corporation) in which a mapping catheter is provided having a basket assembly with a number of circumferentially spaced apart, outwardly bowed, arms, on each of which is mounted a number of mapping electrodes. This enables the isochronal activation map to be rapidly constructed, in substantially one deployment of the mapping catheter and at the identical point in the cardiac cycle.

A problem with such mapping techniques is that the location of the active site can only be inferred from the map so constructed, in the same way the location of a mountain peak may be inferred from a normal isometric contour map.

This problem is mitigated in a system for locating the position of an electrically active site in the heart which is described in U.S. Pat. No. 5,433,198 (Desai). The system disclosed therein has a surface ECG monitor; a cluster of electrical activity sensors for detecting the arrival of an electrical signal from a cardiac site of interest and means for estimating the location of the cardiac site by computing displacement vector. The length of this vector depends on the arrival time of the signal at each of the sensors and on a "difference" time which is an estimation of the time difference between the detection of the signal by an electrode at the point of origin of the signal and the detection of the same signal by the surface ECG monitor. Because this difference time is only an estimation, the length of the displacement vector (and hence the location of the cardiac site) is also only an estimation. As disclosed in this patent this difference time may be between typically −44 and −40 msec, the minus sign indicating that the signal is detected by the surface ECG monitor after its detection by the sensor. Using the embodiment described, this could give an error in the location of the cardiac site of ±2.5 mm, which is of the order of magnitude of the size of the site itself.

SUMMARY OF THE INVENTION

It is an object of the present invention, to provide an apparatus in which the location of an active site relative to a reference frame established by electrical activity sensors can be directly determined by triangulation without the need to create and analyze isochronal maps and without having to make an estimation of the difference time.

The above object is achieved in accordance with the invention in an apparatus for locating an electrically active site within an internal body structure having a number of electrical activity sensors respectively adapted for intracorporeal positioning proximate the internal body structure, each sensor emitting an output signal indicative of the arrival of an electrical signal from the active intracorporeal body site, and having a processor which receives the respective output signals from the activity sensors and which processes these received signals to determine, by triangulation, the location of the intracorporeal active site.

Preferably the electrical activity sensors are mounted on a catheter of a known or determinable shape. This enables the sensors to introduced into and removed from the body with a minimum of invasive surgery in order to form a known or determinable reference frame.

A number of acoustic, electromagnetic or electrical transceivers, for example ultrasonic transceivers, can be disposed along the portion of the catheter on which the sensors, are mounted in known spatial relationship with the sensors and which are operable so that their absolute or relative positions can be determined. From this determination the shape of the catheter and the location of the sensors can then be determined. Conveniently, the electrical activity sensors can be constructed to function also as the transducers and their relative location can be determined from electrical signals emitted and received between the plurality of sensors.

A method of locating catheter mounted transducers within a body which is well known is sonomicrometry and is disclosed, for example, in the above mentioned patent U.S. Pat. No. 5,391,199; in PCT Application WO 98/00060 (Siemens Elema AR); and in U.S. Pat. No. 5,515,853 (Sonometrics Corporation) the contents of all of which are incorporated herein by reference. PCT Application WO 98/00060 describes a method for locating a catheter by transmitting ultrasonic or magnetic signals between a transducer on the catheter and a number of transducers at known reference locations and then analyzing the received signals to determine the length of their transmission paths and hence the location of the catheter by triangulation. Similarly U.S. Pat. No. 5,515,853 discloses an ultrasound catheter tracking system in which the transit times of short duration ultrasound pulses are measured using clocked digital counters and the location of the tracked catheter is again determined using triangulation.

Thus by operating each transceiver of the transceivers of the present invention in turn as an emitter with the remainder of transceivers acting as receivers a signal may be emitted for receipt by all of the other transceivers. By analyzing the received signals to determine transmission path lengths the location of each emitting transceiver relative to all other transceivers can be calculated using standard triangulation methods and a relative reference frame can be established.

The above object is also achieved in accordance with the present invention in a method for locating an electrically active site within an organ, especially the heart, or other bodily structure including the steps of placing electrical activity sensors proximate with, preferably in contact with, a wall of the organ, in particular the heart, or internal bodily structure to establish a reference frame; monitoring each sensor for an output indicative of the arrival of an electrical signal from the active site; processing the outputs to provide an indication of transit times of the electrical signal from the active site to each sensor; and determining by triangulation the location of the active site from the indicated transit times.

Clearly, if the location of the reference frame is known or can be determined then the absolute location of the active site also can be determined from a knowledge of its location relative to the reference frame.

DESCRIPTION OF THE DRAWINGS

FIG. 1 shows a schematic representation of an apparatus according to the present invention introduced into a heart.

FIG. 2 shows an enlargement of a portion of another embodiment of a catheter for use in the inventive method and apparatus.

DESCRIPTION OF THE PREFERRED EMBODIMENTS

In FIG. 1 a location catheter 1 and an ablation catheter 2 are positioned in the left chamber 3 and the right chamber 4, respectively, of a heart 5. As will be clear to those skilled in the art from the further description of the embodiment of FIG. 1, the location catheter 1 and the ablation catheter 2 can be placed in the same heart chamber 3 or 4, depending on the medical procedure to be carried out, without departing from the invention.

The location catheter 1 is provided, in use, with an arcuate section 6 on which is mounted a number of electrical activity sensors, that are in this embodiment electrical transceivers 7a . . . 7n. Catheters which are suitable for use in the apparatus of the present invention are well known in the art, such as the basket or loop or helical type formed, for example, from shape memory material and described in PCT Application WO 98/00060. The shaped section 6 of the location catheter 1 can, of course, be other than arcuate (see FIG. 2) so long a stable platform is provided for the activity sensors 7a . . . 7n on which they can be mounted to form, in use, a two dimensional array of sensors which may be employed for triangulation measurements. It will be appreciated that such location catheters 1 represent a convenient way of introducing the sensors 7a . . . 7n to the heart. There are, however, a number of alternative methods of achieving the accurate location of the sensors 7a . . . 7n proximate the heart wall apparent to those skilled in the art. The sensors 7a . . . 7n could, for example, be directly attached to an external wall of the heart using procedures common in the art and still within the scope of the invention.

The apparatus shown in FIG. 1 also includes a control unit 8 in operable connection with the transceivers 7a . . . 7n and with a signal processor, such as a suitably programmed personal computer, 9. The processor 9 also being operably connected to an ablation unit 10 and a visual display unit 11.

The transceivers 7a . . . 7n can be operated by the control unit 8 to detect electrical signals emitted from an electrically active site, the position of which is to be determined, during, for example, VT. Additionally, the transceivers 7a . . . 7n are each operated by the control unit 8 individually to emit an electrical signal for receipt by the other transceivers, which are then be used to determine their relative positions and thus the shape of the arcuate section 6, as required. This determination need only be made upon deployment or re-deployment of the transceivers 7a . . . 7n.

Alternatively, if the shape of the section 6 of the catheter 1 is a predetermined shape in use then the relative positions of the activity sensors 7a . . . 7n will be fixed and known. This will be useful as it may reduce the signal processing demands on the processor 9 and accelerate the determination of the location of the active site S.

In use, the control unit 8 is operable to vary the function of each of the transceivers 7a . . . 7n between functioning as emitters and receivers. Additionally, the control unit 8 is adapted to receive signals from each of the transceivers 7a . . . 7n that are indicative of the arrival at that transceiver of electrical signals from either another transceiver or from the site S, and to emit to the signal processor 9 information relating to the arrival of the signal, and to the identity of the receiving transceiver 7a . . . 7n. The signals from the transceivers and from the site S can be differentiated from each other (individually identified) simply by controlling the unit 8 to have the transceivers 7a . . . 7n act as emitters only when the heart is functioning normally, as may be indicated for example by a signal input to the processor 9 by a conventional surface ECG electrode 13 and ECG monitor 14 arrangement. Alternatively the control unit 8 operate each transceiver 7a . . . 7n to emit an electrical signal at a frequency sufficiently removed from that of the signal from the active site S to allow a differentiation between the signals based on their frequencies to be made using known de-multiplexing circuitry.

This information is then used by the processor 9 to determine the arrival time of the electrical signal at each of the transceivers 7a . . . 7n relative to a reference time, which can be provided by the earliest detection of the electrical signal by a transceiver (such as, for example, 7n) when the electrical signal originates from the site S, or which may be the time at which a transceiver is activated to emit an electrical signal.

Using the appropriate arrival times and associated reference time and with a knowledge of the relative locations of each of the transceivers 7a . . . 7n of the location of the site S can be determined by triangulation using computer algorithms easily created by those skilled in the art. As described above, the relative locations can be deduced from a prior knowledge of the shape the arcuate section 6 will attain in use or may be determined using the signal processor 9. In this latter case, the processor 9 can command the control unit 8 to operate a transducer (for example 7a) as an emitter to emit a signal for receipt by each of the remaining transceivers 7b . . . 7n. Using the time at which the transceiver 7a is activated as the reference time the arrival times at each of the other transmitters 7b . . . 7n can be derived and their positions relative to the transceiver 7a determined by triangulation employing the signal processor 9 in a manner analogous to that for the determination of the location of the active site S. This can then be repeated with the control unit 8 operating each of the remaining transducers 7b . . . 7n in turn as emitters. Thus the location of each transducer with respect to each of the other transducers of the group of transducers 7a . . . 7n can be determined by the signal processor 9. This enables the shape of the arcuate section 6 to be determined if required.

FIG. 2 illustrates an alternative location catheter 15 in which ultrasonic signals are used to determine the relative locations of the electrical activity sensors 7a . . . 7n. Here each sensor 7a . . . 7n is mounted on a respective tine 16a . . . 16n which can be pushed out of the open end 17 of the catheter 15 after insertion of the catheter 15 into the heart or other internal bodily structure of interest. Ultrasonic transceivers 18a . . . 18n are also mounted, one on each tine 16a . . . 16n, at a known distance from its co-mounted sensor 7a . . . 7n. Each transceiver, for example 18a, may be operated in turn to act as an emitter to generate an ultrasound signal for receipt by the remaining ultrasound transceivers, for example 18b . . . 18n. The received signals can then be used to determine the location of the transceiver 18a with respect to the other transceivers 18b . . . 18n by triangulation and similarly for all combinations of emitters and receivers. The relative locations of each of the sensors 7a . . . 7n can then be determined. This can be achieved using a suitably modified control unit 8 and processor 9 or dedicated electronics 19 may be provided, as is used in known ultrasonic sonomicrometry systems to make this determination and to emit a signal indicative of the locations for use by the processor 9.

Once the location of the active site S is determined the ablation catheter 2 can be guided to that site, which can then be ablated.

Guidance of the ablation catheter 2 can be done using conventional ultrasonic sonometric techniques. Preferably however, a location electrical signal emitter 12 can be located proximate the tip of the ablation catheter 2 and operated to emit an electrical signal that can detected by the transceivers 7a . . . 7n.

Again, the detected signal is transmitted to the control unit 8 which provides an output to the signal processor 9 indicating the receipt of the signal and the identity of the transceiver 7a . . . 7n which received it. The signal processor 9 may then determine the location of the emitter 12 relative to the transceivers 7a . . . 7n by triangulation using the same algorithms employed in determining the location of the site S as well as the relative positions of the transceivers 7a . . . 7n, but here using the time of operation (activation) of the emitter 12 as the reference time.

The relative positions of the active site S and the emitter 12 (or more conveniently the tip of the ablation catheter 2) can be supplied from processor 9 and displayed on the display unit 11 as a guidance aid to an operator. Additionally, as is also common in the art of sonomicrometry, these relative locations can be displayed on the monitor 11 overlaid on an image of the heart 5 obtained by conventional imaging techniques.

Once the ablation catheter 2 is at the site S the processor 9 can operate the ablation unit 10 to energize the ablation catheter 2. Alternatively, the processor 9 can issue a signal to permit the manual operation of the ablation unit 9 to energize the catheter 2. Thus the processor 9 can act as a safety switch to minimize the risk of erroneously energizing the ablation catheter 2 away from the active site S.

While the embodiment of the present invention has been described as a possible implementation those skilled in the art will understand that variations thereof will be possible while still falling within the scope of the claimed invention.

For example, if only a determination of the location of the active site S is needed then the ablation or other treatment of the active site will not be required. The presence of the ablation catheter 2 and associated equipment 10 and related processor functionality would be therefore be obviated. Furthermore, if ultrasonic transducers 18a . . . 18n are co-mounted with the electrical activity sensors 7a . . . 7n then the emitter 12 used to locate the catheter 2 can be an ultrasonic emitter (or receiver) which could cooperate with the transducers 18a . . . 18n in order to determine the location of the tip of the catheter 2.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for locating an electrically active site within an internal body structure comprising:

a plurality of electrical activity sensors respectively adapted for intracorporeal positioning proximate an internal body structure;

each sensor emitting an output signal indicative of an arrival of an electrical signal from an active intracorporeal body site; and a processor which receives the respective output signals from said electrical activity sensors, as received signals, and which processes said received signals to determine, by triangulation, a location of said active site.

2. An apparatus as claimed in claim 1 further comprising a catheter adapted for intracorporeal insertion proximate said internal body structure, said plurality of electrical activity sensors being carried on said catheter.

3. An apparatus as claimed in claim 2 wherein said catheter has an arcuate section along which said electrical activity sensors are mounted.

4. An apparatus as claimed in claim 3 wherein said arcuate section comprises a controllably deformable section of said catheter, said controllably deformable section being deformable into an arcuate shape after introduction of said catheter into a body.

5. An apparatus as claimed in claim 2 further comprising a plurality of transceivers mounted along said catheter and having known respective spatial relationships to said activity sensors in said plurality of activity sensors, said plurality of transceivers being individually operable to emit an energy signal for receipt by all other transceivers in said plurality of transceivers, and wherein said processor receives said energy signals and determines from the received energy signals the locations of the respective transceivers by triangulation.

6. An apparatus as claimed in claim 5 wherein said plurality of electromagnetic transceivers are selected from the group of transceivers consisting of electromagnetic transceivers, electrical transceivers and acoustic transceivers.

7. An apparatus as claimed in claim 5 wherein said plurality of electrical activity sensors comprise said plurality of transceivers.

8. An ablation system comprising:

a plurality of electrical activity sensors respectively adapted for intracorporeal positioning proximate an internal body structure;

each sensor emitting an output signal indicative of an arrival of an electrical signal from an active intracorporeal body site;

a processor which receives the respective output signals from said electrical activity sensors, as received signals, and which processes said received signals to determine, by triangulation, a location of said active site; and an ablation catheter directable to said active site dependent on an output signal from said processor corresponding to the location of the active site obtained by triangulation.

9. A method of locating an electrically active site within an internal body structure, comprising the steps of:

intracorporeally placing a plurality of electrical activity sensors proximate an internal body structure, each of said electrical activity sensors emitting an output signal indicative of an arrival of an electrical signal from an active intracorporeal site;

monitoring each of said electrical activity sensors for emission of said output signal;

processing the respective output signals from said electrical activity sensors to identify respective transit times of said electrical signal from said active intracorporeal site to each of said electrical activity sensors; and identifying relative locations of each of said electrical activity sensors and determining by triangulation and said transit times a location of said active intracorporeal site relative to said electrical activity sensors.

* * * * *